US007550638B2

(12) United States Patent
Bridges et al.

(10) Patent No.: US 7,550,638 B2
(45) Date of Patent: Jun. 23, 2009

(54) INTEGRATED CRACKING AND METATHESIS PROCESS

(75) Inventors: Robert S. Bridges, Friendswood, TX (US); Steven T. Coleman, Humble, TX (US)

(73) Assignee: Equistar Chemicals, LP, Houston, TX (US)

( * ) Notice: Subject to any disclaimer, the term of this patent is extended or adjusted under 35 U.S.C. 154(b) by 541 days.

(21) Appl. No.: 11/280,789

(22) Filed: Nov. 16, 2005

(65) Prior Publication Data

US 2007/0112236 A1    May 17, 2007

(51) Int. Cl.
  C07C 6/04    (2006.01)
  C07C 2/06    (2006.01)
(52) U.S. Cl. .................. 585/324; 585/329; 585/330; 585/646; 585/647; 585/643; 585/512; 585/513
(58) Field of Classification Search .................. 585/324, 585/329, 330, 646, 647, 643, 512, 513
See application file for complete search history.

(56) References Cited

U.S. PATENT DOCUMENTS 3,485,881 A    12/1969  Zuech ........................ 260/666
3,627,700 A    12/1971  Zuech ...................... 252/429 B
3,726,939 A     4/1973  Zuech ........................ 260/683
5,435,904 A *   7/1995  Reed et al. ............... 208/48 AA
5,898,091 A     4/1999  Chodorge et al. ........... 585/647
2005/0107650 A1 5/2005  Sumner ....................... 585/324

FOREIGN PATENT DOCUMENTS

CN          1373007 A    * 10/2002
WO  PCT/US2006/041613      10/2006

OTHER PUBLICATIONS

"Hydrocarbon Processing—Petrochemical Processes" Hydrocarbon Processing, Gulf Publishing Co., Houston, US, Mar. 2003, pp. 70-126, XP002322126, ISSN: 0018-8190, p. 126, left column, second paragraph.

* cited by examiner

*Primary Examiner*—Thuan Dinh Dang
(74) *Attorney, Agent, or Firm*—Roderick W. MacDonald

(57) ABSTRACT

An integrated method that comprises a hydrocarbon thermal cracking operation to form at least one olefin product, coupled with dimerization and metathesis operations, the dimerization operation forming additional feed material for the metathesis operation, and the metathesis operation forming additional amounts of olefin product.

7 Claims, 3 Drawing Sheets

INTEGRATED CRACKING AND METATHESIS PROCESS

BACKGROUND OF THE INVENTION

This invention relates to the thermal cracking and disproportionation (metathesis) of hydrocarbons in an integrated method. More particularly, it relates to the thermal cracking of ethane to form, in part, ethylene, and the disproportionation of 2-butene in the presence of ethylene to form propylene.

DESCRIPTION OF THE PRIOR ART

Thermal cracking of hydrocarbons is a petrochemical process that is widely used to produce olefins such as ethylene, propylene, butenes, butadiene, and aromatics such as benzene, toluene, and xylenes. In an olefin production plant, a hydrocarbonaceous feedstock such as ethane, naphtha, gas oil, or other fractions of whole crude oil is mixed with steam which serves as a diluent to keep the hydrocarbon molecules separated. This mixture, after preheating, is subjected to severe hydrocarbon thermal cracking at elevated temperatures (1,450 to 1,550 degrees Fahrenheit or F.) in a pyrolysis furnace (steam cracker or cracker).

The cracked product effluent of the pyrolysis furnace (furnace) contains hot, gaseous hydrocarbons of great variety (from 1 to 35 carbon atoms per molecule, or $C_1$ to $C_{35}$, inclusive). This product contains aliphatics, alicyclics, aromatics, saturates, and unsaturates, and molecular hydrogen (hydrogen).

This furnace product is then subjected to further processing to produce, as products of the olefin plant, various, separate and individual product streams such as hydrogen, ethylene, propylene, fuel oil, and pyrolysis gasoline. After the separation of these individual streams, the remaining cracked product contains essentially $C_4$ hydrocarbons and heavier. This remainder is fed to a debutanizer wherein a crude $C_4$ stream is separated as overhead while a $C_5$ and heavier stream is removed as a bottoms product.

Such a $C_4$ stream can contain varying amounts of n-butane, isobutane, 1-butene, 2-butenes (both cis and trans isomers), isobutylene, acetylenes, and diolefins such as butadiene (both cis and trans isomers).

Separately from the cracking process aforesaid, crude $C_4$ streams have heretofore been subjected to selective hydrogenation of diolefins to convert them to the corresponding monoolefins with simultaneous isomerization of alpha olefins to internal olefins followed by etherification of the isoolefins, and finally metathesis of internal olefins with ethylene to produce propylene, U.S. Pat. No. 5,898,091.

Also separately from the cracking process aforesaid, ethylene has been dimerized followed by a metathesis operation to form polymer grade propylene.

It is advantageous for a number of reasons which will be discussed hereinafter in detail, to have a single, integrated process which employs cracking, dimerization, and metathesis therein, particularly when directed to the formation of ethylene and propylene products.

SUMMARY OF THE INVENTION

In accordance with this invention a single, integrated process is provided which cracks a hydrocarbon such as an ethane containing feed to form at least one product olefin, metathesizes internal olefins to form additional product olefin, and internally generates additional feed for the metathesis operation. This method has the flexibility to produce an ethylene product, or a propylene product, or both, all from ethane.

DETAILED DESCRIPTION OF THE INVENTION

Figure 1:
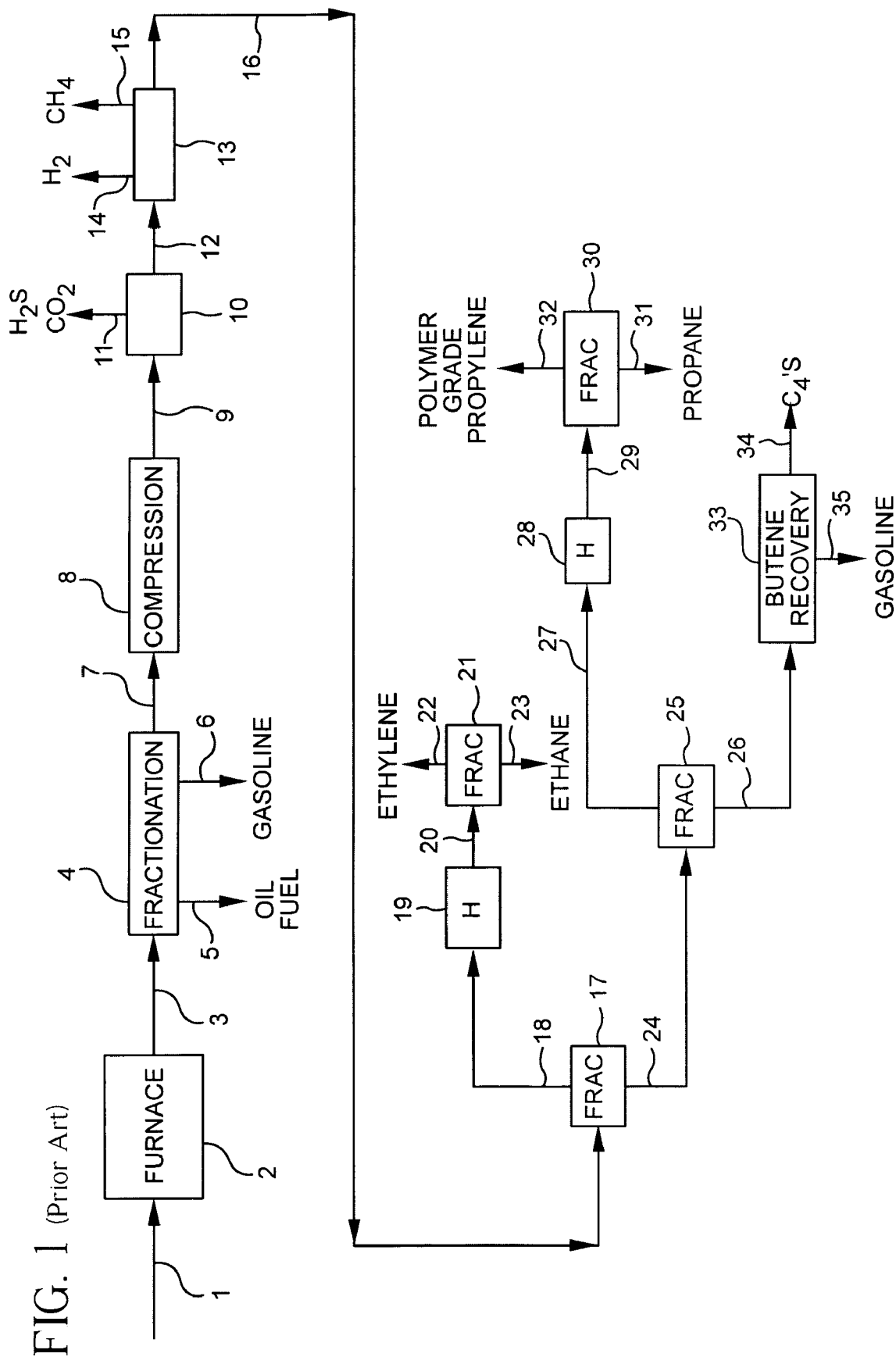
FIG. 1 is a flow diagram of a conventional hydrocarbon cracking plant that produces polymer grade propylene.

FIG. 1 shows a typical cracking plant wherein a hydrocarbonaceous feed 1 is introduced into a thermal cracking furnace 2. It should be noted that there are many other cracking plant processing configurations than that shown in FIG. 1. This invention is applicable to all such other configurations, FIG. 1 being just a single example of an applicable configuration. In furnace 2, a plurality of differing hydrocarbon compounds are formed as aforesaid to produce a cracked product 3. Hot, gaseous effluent 3 invariably includes, among many other compounds, ethylene, propylene, and butenes, both alpha (1-butene) and internal (2-butenes). Product 3 is subjected to separate oil and water quenches and other fractionation, collectively unit 4, to liquefy heavier compounds ($C_5$ and heavier) therein to form liquid streams such as fuel oil stream 5 and automotive gasoline grade (pyrolysis gasoline) stream 6, which streams are removed from the overall cracking process for other use elsewhere. The gaseous product 7 of fractionation operation 4 is transferred to a compression zone 8 wherein it undergoes several stages of compression. The compressed product 9 then undergoes a process 10, such as caustic washing, to remove acid gases therefrom, including hydrogen sulfide and carbon dioxide 11. The product 12 of zone 10 passes to a separation zone 13 which is a combination of cryogenic cooling and fractional distillation, and from which is separated a high purity molecular hydrogen stream 14 and a separate methane stream 15, both of which are removed as products of the overall cracking plant.

The remainder of effluent 3 is transferred by way of line 16 to fractional distillation zone 17 wherein ethane and ethylene are separated and recovered in line 18, with the remainder of stream 16 being recovered as bottoms 24.

Stream 18 is subjected to selective hydrogenation step 19 to convert acetylenics and diolefins to their corresponding monoolefins, after which it is passed by way of line 20 to another fractional distillation zone 21 wherein ethylene is separated from ethane, and each are recovered as separate products 22 and 23, respectively, of the cracking plant.

Stream 24 is also subjected to additional fractional distillation in zone 25 to separate propane and propylene therefrom as an overhead stream 27, and leave a $C_4$ containing stream 26 as a bottoms product.

Stream 27 is subjected to selective acetylenic and diolefin hydrogenation to convert same to their corresponding monoolefins in zone 28, and the resulting hydrotreated stream 29 passed to a fractional distillation zone 30 wherein propane is separated from propylene to form separate streams 31 and 32, both of which are removed as products of the overall cracking process.

Propylene product 32 is a very pure polymer grade material. As such, product 32 has a propylene content that is substantially greater than that of chemical grade propylene. Chemical grade propylene has numerous uses of value. In fact, most processes involving propylene and outside the polymer industry, e.g., the production of propionitrile, propylene oxide, and the like, requires only chemical grade propylene. The use of polymer grade propylene in such processes is neither practical nor necessary. The separation of propane from propylene in tower 30 is quite difficult due to the close proximity of their respective boiling points. Accordingly, distillation column 30 is very large in size, and is expensive as to both its construction and operating costs. If a process produced chemical grade propylene it would have enhanced flexibility because the chemical grade material could, if desired, be transformed into polymer grade material, or it could be used, without more, in the numerous commercial processes that call for chemical grade propylene. This invention provides that flexibility.

Stream 26 is subjected to a butene recovery fractional distillation process in zone 33 wherein a $C_4$ containing stream 34 is separated as a product of the overall cracking process. The $C_5$ and heavier materials in stream 26 are separated as stream 35 for various uses such as addition to the automotive gasoline pool.

Thus, the cracking plant of FIG. 1 produces, among other materials, ethane, ethylene, polymer grade propylene, and propane, with essentially no flexibility for doing otherwise.

Figure 2:
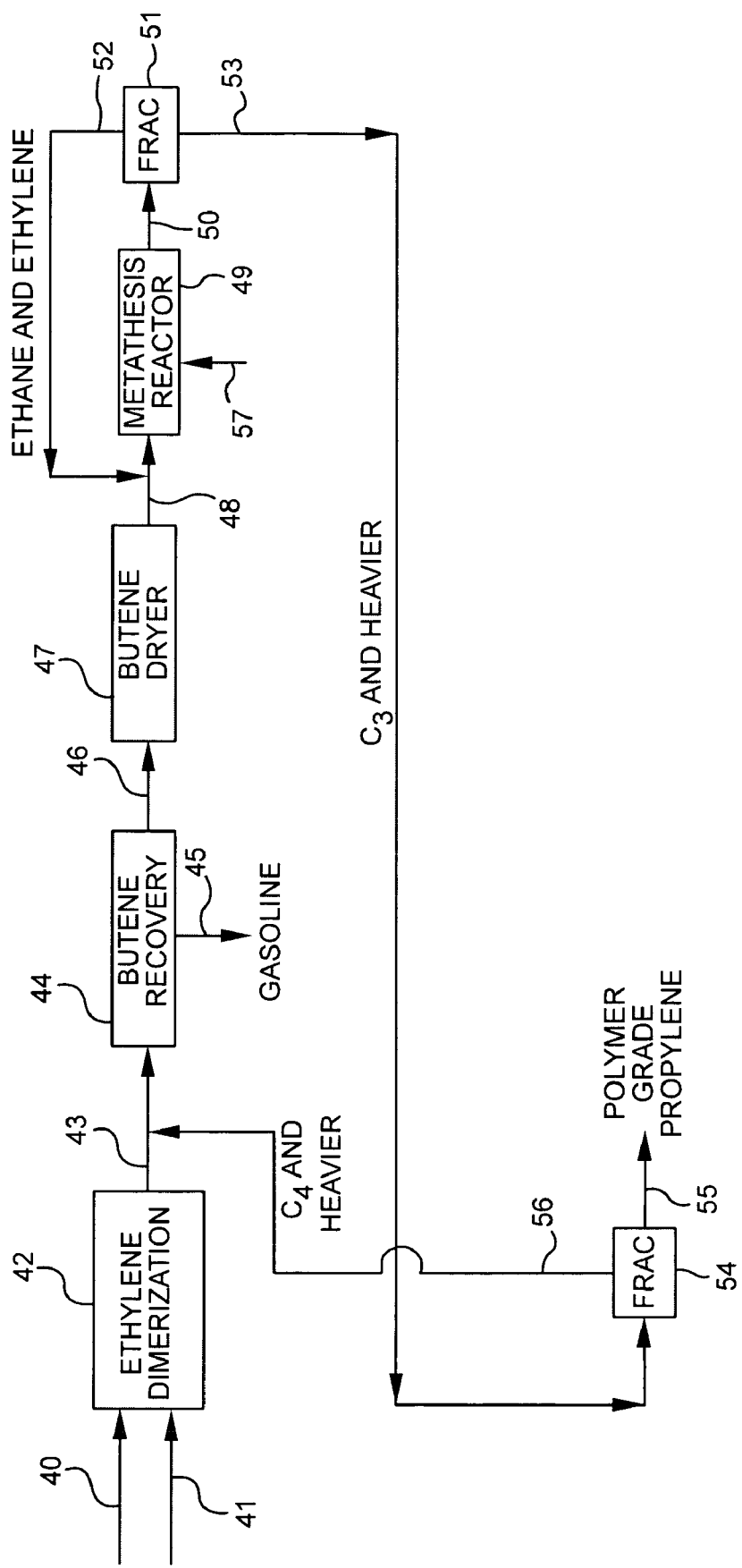
FIG. 2 is a flow diagram of a conventional ethylene dimerization plant that employs a metathesis unit to produce polymer grade propylene.

FIG. 2 shows a particularly useful commercial process known as "Product Flexibility" as employed in its dimer mode. In this Figure, ethylene feed 40 and catalyst 41 are fed into ethylene dimerization reactor 42 which is maintained under conditions that favor the dimerization of ethylene to butenes, 2-butenes being favored over 1-butene. The butene containing product 43 of reactor 42 is passed to butene recovery zone 44 wherein an automotive grade gasoline stream 45 is separated therefrom, and a $C_4$ rich stream 46 is produced. Butene stream 46 is subjected to a drying step 47 to prepare it for use as feed 48 to metathesis zone 49. Additional ethylene feed 57 can be employed if necessary to ensure an excess of ethylene is present. The product 50 of reactor 49 is passed to fractional distillation zone 51 wherein ethane and ethylene are separated therefrom and returned as feed to reactor 49 by way of line 52. The $C_3$ and heavier materials are passed by way of line 53 to a fractional distillation zone 54. In zone 54, polymer grade propylene 55 is separated out as a product of the overall dimerization/metathesis process, the remaining $C_4$ and heavier materials being returned by way of line 56 as feed to butene recovery zone 44.

Figure 3:
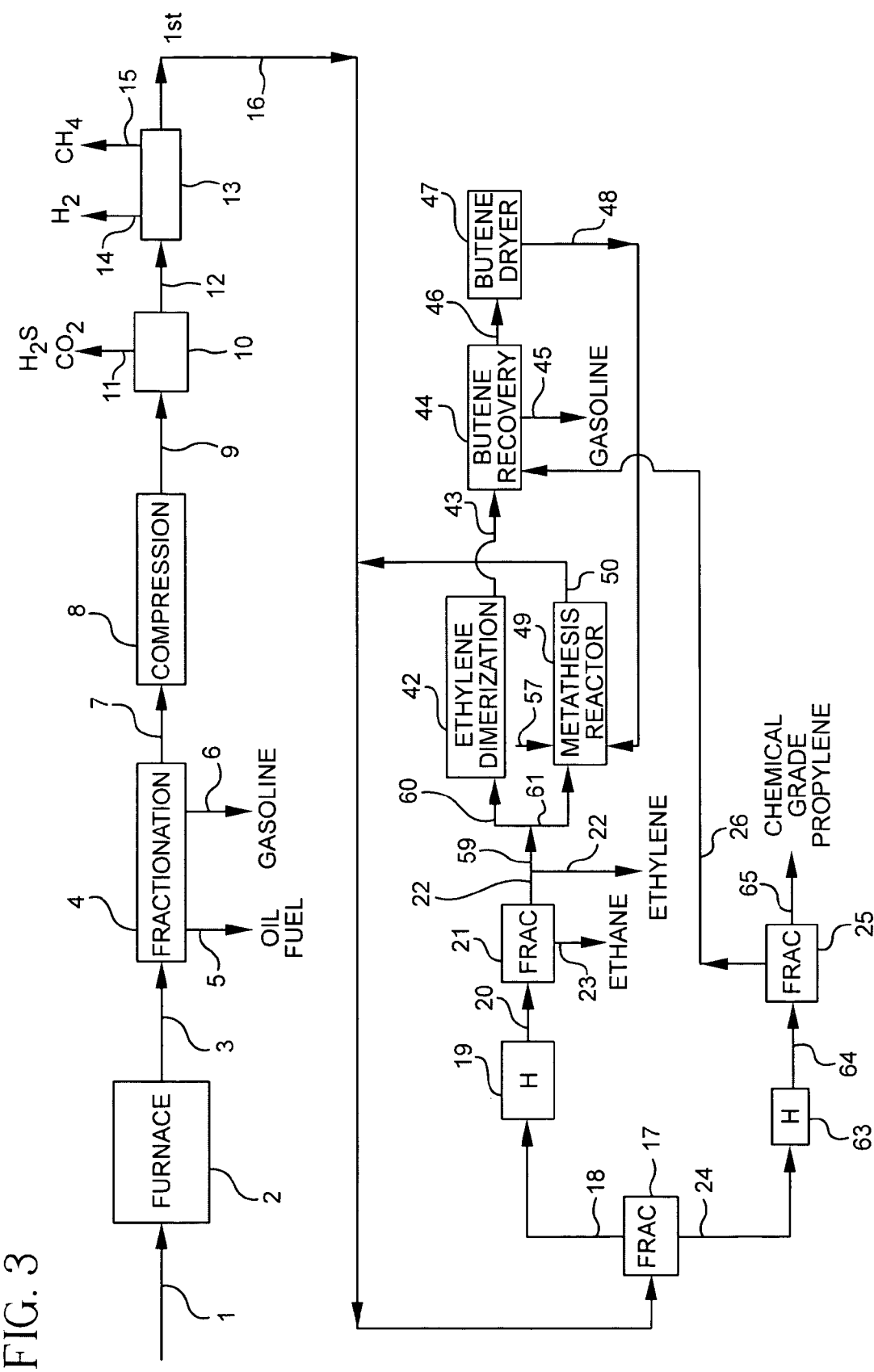
FIG. 3 is a flow diagram that demonstrates one embodiment within this invention that produces chemical grade propylene.

FIG. 3 employs units of both FIGS. 1 and 2. For sake of clarity, the reference numbers used in FIGS. 1 and 2 are carried over to FIG. 3 for those units that are present in FIGS. 1 and 2, and are carried over into FIG. 3. Accordingly, elements 1 through 16, inclusive, in FIG. 3 are identical to the elements similarly marked in FIG. 1, and will not, for sake of brevity, be described in greater detail at this point because the process is well known, and further detail is not necessary to inform one skilled in the art. At line 16, this invention starts to take over.

Fractionation zone 17 is the same unit as set forth in FIG. 1 but has a different feed thereto because of the addition of the stream in line 50 which will be discussed in more detail hereinafter. In this invention, zone 17 also separates an overhead stream 18 that contains essentially ethane and ethylene, leaving the remainder of stream 16 as a bottoms product stream 24.

Stream 24 is subjected in zone 63 to selective hydrogenation of its acetylenic and diolefinic components to monoolefins as aforesaid. The hydrogenated product 64 is then passed to fractional distillation zone 25 wherein a chemical grade propylene product 65 is recovered as a product of the overall integrated process of FIG. 3. The remainder of stream 64 is recovered from zone 25 and passed to butene recovery zone 44, see FIG. 2.

Stream 18 is passed to a selective hydrogenation zone 19, followed by fractional distillation in zone 21, just as explained hereinabove for FIG. 1. At this point this invention really takes over. An ethane product stream 23 can, if desired, but is not required, be recovered as in FIG. 1, but, in any event, ethylene stream 22 is treated much differently in this invention. If desired, of course, a relatively pure ethylene product stream 22 can be removed from the overall process, but, in accordance with this invention, some, even a substantial amount, if not all, of stream 22 can be passed into line 59. In addition to, or in lieu of, stream 59 containing all or part of the contents of stream 22, stream 59 can contain, for example, in whole or in part 1) a side draw of an impure ethylene stream from unit 21 (e.g., an impure ethylene stream taken from the tower above the feed but below the product stream 22), and/or 2) ethylene fractionation feed stream 20.

Stream 59 is split between lines 60 and 61. The relative amounts that go into steams 60 and 61 can vary widely depending on how the process is desired to be operated at any given time, it only being required that some of stream 59 goes into each of streams 60 and 61. However, at least about 67 wt. %, but less than all, of stream 59 can go into stream 60 and about 33 wt. %, but less than all, can go into stream 61, both wt. % based on the total weight of stream 59.

Stream 60 passes to ethylene dimerization zone 42, while stream 61 is passed to metathesis reactor 49, compare with FIG. 2. The operation of zones 42 and 49 are the same as in FIG. 2, zone 42 producing a stream 43 that is rich in butenes, and zone 49 producing a propylene containing stream 50. As in FIG. 2, additional ethylene feed can be supplied by way of line 57, if desired.

Propylene rich stream 50 from reactor 49 is added to stream 16, and after processing in units 17 and 63, the propylene newly formed in zone 49 finds its way to zone 25, and, therefore, to propylene product stream 65.

Stream 43 passes to butene recovery unit 44, from which is separated an automotive grade gasoline stream 45. The butenes rich product 46 is subjected to drying in unit 47 to prepare it as feed for disproportionation, and then passed by way of line 48 as feed to metathesis reactor 49.

A comparison of FIGS. 1-3 shows that large and expensive fractionation tower 30 and butene recovery unit 33 of FIG. 1 have been eliminated by this invention without eliminating the function thereof. This same comparison shows that fractionation towers 51 and 54 of FIG. 2 have similarly been eliminated without loss of their function. Although this comparison will also show that selective hydrogenation zone 28 of FIG. 1 is not present in FIG. 3, this function has not been eliminated because a new selective hydrogenation zone 63 (FIG. 3) is employed in this invention.

Thus, it can be seen that a major advantage of this invention is the elimination of the difficult and costly operation of separating propane from propylene (tower 30). This results in a substantial savings in both construction and operating costs. But this is not the only advantage. A significant advantage for this invention is the gain in flexibility of operation in a number of ways. There is greater product flexibility because this invention produces a chemical grade propylene product, the grade that most processes require, without losing the ability to upgrade to the more pure polymer grade of propylene later, if desired. This invention also provides the flexibility to significantly vary the relative production volumes of ethylene and propylene from an ethane cracking plant. This invention also provides the flexibility to produce a propylene product from a plant that cracks a feedstock that contains essentially only ethane. Finally, flexibility is improved in that the metathesis reactor has two sources of ethylene feed, i.e., from the cracking operation itself and from any residual ethylene from dimerization unit 42.

The disproportionation reaction employed in reactor 49 is well known. It is a double displacement mechanism that starts with two different compounds. The reaction involves the displacement of groups from each compound to produce two new compounds. There is displacement cleavage at a double bond on each different compound, and the new compounds have double bonds where the old double bonds were cleaved. Thus, the metathesis of one mole of 2-butene and one mole of ethylene yields two moles of propylene. These reaction conditions can vary widely, but generally will include a temperature of from about 300 to about 800 F., a pressure of from about 200 to about 600 psig, and a weight hourly space velocity of from about 1 to about 100 reciprocal hours (based on butene and tungsten trioxide catalyst). Suitable catalysts that favor the disproportionation reaction include at least one of halides, oxides and/or carbonyls of at least one of molybdenum, tungsten, rhenium, and/or magnesium carried on an acidic support such as alumina, silica, alumina/silica, zeolites, and the like. This process is in commercial use, and further detail is not necessary in order to inform the art.

The ethylene dimerization reaction is a homogeneous liquid phase reaction that is also well known, and in commercial use. Its reaction conditions will also vary widely, but will generally include a temperature of from about 80 to about 150 F., a pressure of from about 100 to about 300 psig, and a residence time of from about 15 to about 60 minutes. Suitable catalysts that favor the homogeneous liquid phase dimerization reaction include at least one from the aluminum alkyl halide family, such as ethyl aluminum dichloride, and a nickel salt-phosphine complex. This process is well known, see U.S. Pat. Nos. 3,485,881; 3,627,700; and 3,726,939.

EXAMPLE

A feed consisting essentially of ethane with less than 10 weight percent (wt. %) of impurities such as propane is cracked at a temperature of from about 1,500 to about 1,600 F. at a pressure of from about 15 to about 25 psig. The cracked product is cooled and then subjected to oil quenching followed by water quenching to a temperature of about 100 F. at about 10 psig, after which it is subjected to compression to a pressure of about 520 psig. The compressed stream is cooled to about 60 F., dried, and then chilled and partially condensed in stages to a temperature of at least about minus 240 F. to separate from the compressed stream a high purity hydrogen stream. Methane is next separated from the remaining hydrocarbons via distillation as an overhead product from a demethanation tower.

This cracked product (16, FIG. 3) from the bottoms of the demethanizer is passed to distillation tower 17 which operates at a bottom temperature of about 170 F. at a pressure of about 350 psig to form an overhead stream that consists essentially of ethane and ethylene, line 18, and a bottoms stream 24 that contains $C_3$ and heavier hydrocarbons.

Stream 24 is subjected to selective hydrogenation 63 at a temperature of about 100 F., a pressure of about 300 psig, and a weight hourly space velocity of about 10 reciprocal hours, using a catalyst composed of palladium on an aluminum support. Thereafter the hydrogenated stream is distilled at a bottom temperature of about 200 F. and 110 psig to separate out an overhead product 65 that consists essentially of chemical grade propylene.

Stream 18 is selectively hydrogenated using similar conditions and catalyst used on stream 24 followed by distillation of the hydrogenated stream in a tower with a bottom temperature of about 20 F. and pressure of about 280 psig to remove a stream consisting essentially of ethane therefrom, and leaving a separate stream 22 consisting essentially of ethylene.

About 50 wt. % of ethylene stream 22 is removed as product of the overall process. The remainder of stream 22 is split, about 67 wt. % to stream 60 and about 33 wt. % to stream 61. All wt. % are based on the total weight of the stream.

Stream 60 is passed to an ethylene dimerization reactor operating at a temperature of about 100 F., a pressure of about 150 psig, and a residence time of about 30 minutes, using a mixture of ethyl aluminum dichloride and a nickel salt-phosphine complex to catalyze the reaction. After quenching the reaction and removing residual catalyst, the dimerized product 43 is subjected to fractional distillation at a bottom temperature of about 230 F. and 70 psig to remove $C_5$ and heavier hydrocarbons as an automotive gasoline product and produce a butene rich stream 46. Stream 46 is dried at ambient temperature and about 60 psig pressure using a molecular sieve adsorbent, and then returned as feedstock to metathesis reactor 49.

Streams 48 and 61 are introduced as feedstock into metathesis reactor 49 which is operated at a temperature of about 600 F., a pressure of about 400psig, and a weight hourly space velocity of about 15 reciprocal hours (based on butenes and the tungsten oxide catalyst), using a catalyst consisting essentially of a mixture of tungsten oxide on a silica support and magnesium oxide. In reactor 49, 2-butene is disproportionated in the presence of an excess of ethylene to form a product 50 that is rich in propylene. This product is combined with cracked stream 16 and the resulting combination stream passed to fractionation zone 17 as feedstock therefor.

We claim:

1. An integrated method for cracking an ethane containing feed and metathesizing ethylene to propylene, comprising thermally cracking said feed to form a first stream (16) containing ethane, ethylene and hydrocarbons heavier than ethane and ethylene and including 2-butenes, subjecting said first stream to a first fractional distillation (17) to form a second stream (18) containing at least some of said ethane and ethylene in said first stream and a third stream (24) containing predominantly said hydrocarbons in said first stream that are heavier than ethane and ethylene, recovering chemical grade propylene (65) from said third stream as a product of the overall process, subjecting a first portion (60) of said second stream to an ethylene dimerization operation to form a dimerization product stream (43) that contains newly formed butenes, subjecting a second portion (61) of said second stream to a metathesis operation wherein 2-butenes are subjected to disproportionation conditions in the presence of ethylene to form a propylene containing stream (50), passing said propylene containing stream from said metathesis operation as feed to said first fractional distillation, passing said dimerization product stream to a butene recovery operation to form a first butene containing stream (48), passing said first butene containing stream as feed to said metathesis operation, separating a second butene containing stream (26) from said third stream, and passing said second butene containing stream to said butene recovery operation.

2. The method of claim 1 wherein an ethylene stream (22) is recovered from said second stream as a product of the overall process.

3. The method of claim 1 wherein said butene containing product (43) from said ethylene dimerization operation contains at least in part 2-butenes that were newly formed in said dimerization operation.

4. The method of claim 1 wherein said 2-butenes that are disproportionated in the presence of ethylene in said metathesis operation are derived from both said thermal cracking (26) and said ethylene dimerization (43).

5. The method of claim 1 wherein said ethylene dimerization conditions include a temperature of from about 80 to about 150 F., a pressure of from about 100 to about 300 psig, and a nonaqueous liquid phase catalyst that favors the dimerization of ethylene.

6. The method of claim 5 wherein said catalyst is selected from the group consisting of aluminum alkyl halides arid nickel salt-phosphine complexes.

7. The method of claim 1 wherein said metathesis conditions include a temperature of from about 300 to about 800 F., a pressure of from about 200 to about 600 psig, a catalyst that favors the disproportionation of 2-butene in the presence of ethylene to propylene, and a weight hourly space velocity of from about 1 to about 100 reciprocal hours.

* * * * *